(12) United States Patent
Hirasaka et al.

(10) Patent No.: US 8,232,434 B2
(45) Date of Patent: Jul. 31, 2012

(54) PROCESS FOR PRODUCING FLUOROALKYL IODIDE TELOMER

(75) Inventors: Takeomi Hirasaka, Osaka (JP); Yoshinori Tanaka, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 66 days.

(21) Appl. No.: 12/935,521

(22) PCT Filed: Mar. 30, 2009

(86) PCT No.: PCT/JP2009/056435
§ 371 (c)(1),
(2), (4) Date: Sep. 29, 2010

(87) PCT Pub. No.: WO2009/123082
PCT Pub. Date: Oct. 8, 2009

(65) Prior Publication Data
US 2011/0028768 A1    Feb. 3, 2011

(30) Foreign Application Priority Data

Mar. 31, 2008    (JP) .................................. P2008-092078

(51) Int. Cl.
*C07C 17/00*    (2006.01)
*C07C 17/266*    (2006.01)
(52) U.S. Cl. .......................... 570/139; 570/169; 570/172
(58) Field of Classification Search .................. 570/139, 570/169, 172
See application file for complete search history.

(56) References Cited

U.S. PATENT DOCUMENTS

| | | | |
|---|---|---|---|
| 5,068,471 A | 11/1991 | Paul et al. | |
| 5,639,923 A | 6/1997 | Von Werner | |
| 5,650,545 A | 7/1997 | Bertocchio et al. | |
| 5,929,292 A | 7/1999 | Shimoyama et al. | |
| 2004/0116753 A1 | 6/2004 | Funakoshi et al. | |

FOREIGN PATENT DOCUMENTS

| | | |
|---|---|---|
| CA | 2166024 A1 | 6/1996 |
| JP | 6-305995 A | 11/1994 |
| JP | 8-239335 A | 9/1996 |
| JP | 8-239336 A | 9/1996 |
| JP | 10-59880 A | 3/1998 |
| JP | 2002-316956 A | 10/2002 |
| JP | 2002-316957 A | 10/2002 |
| JP | 3800677 B2 | 7/2006 |

OTHER PUBLICATIONS

Qing-Yun Chen et al. "Copper-Induced Telomerization of Tetrafluoroethylene with Fluoroalkyl Iodides", Journal of Fluorine Chemistry, vol. 36, pp. 483-489. 1987.
International Preliminary Report on Patentability and English translation of the Written Opinion of the International Searching Authority dated Dec. 23, 2010 for Application No. PCT/JP2009/056435 (Forms PTO/IB/338, PCT/IB/373 and PCT/ISA/237).

*Primary Examiner* — Jafar Parsa
(74) *Attorney, Agent, or Firm* — Birch, Stewart, Kolasch & Birch, LLP

(57) ABSTRACT

A novel process for producing a fluoroalkyl iodide telomer is provided, which is able to obtain a fluoroalkyl iodide telomer having a desired chain length, efficiently.

A fluoroalkyl iodide represented by the general formula RfI (wherein Rf is a $C_{1-10}$ fluoroalkyl group) and tetrafluoroethylene are used as a telogen and a taxogen, respectively. These compounds are supplied to a distillation apparatus. In a reaction zone located in an intermediate part of the distillation apparatus, the compounds are subjected to a telomerization reaction in the presence of a metal catalyst with heating to generate a fluoroalkyl iodide telomer represented by the general formula $Rf(CF_2CF_2)_nI$ (wherein Rf is the same as defined above and n is an integer of 1-4). Thereafter, a fraction comprising the fluoroalkyl iodide telomer is separated by distillation.

6 Claims, No Drawings

PROCESS FOR PRODUCING FLUOROALKYL IODIDE TELOMER

TECHNICAL FIELD

The present invention relates to a process for producing a fluoroalkyl iodide telomer, more specifically to a process for producing a fluoroalkyl iodide telomer by a telomerization reaction while a fluoroalkyl iodide and tetrafluoroethylene are used as a telogen and a taxogen, respectively.

BACKGROUND ART

Fluoroalkyl iodides having a carbon number of about 6-12 are useful compounds as a raw material for a surfactant agent, a raw material for an oil- and water-repellant agent for treating fabrics, and so on.

Such a fluoroalkyl iodide is industrially produced by a telomerization reaction according to the following formula:

$$RfI + nCF_2 = CF_2 \rightarrow Rf(CF_2CF_2)_nI$$

wherein Rf represents a fluoroalkyl group, and n represents a degree of polymerization and is preferably an integer of 1-4, In this telomerization reaction, a fluoroalkyl iodide represented by the general formula RfI is a telogen; tetrafluoroethylene is a taxogen; and a fluoroalkyl iodide represented by the general formula $Rf(CF_2CF_2)_nI$ is a telomer. The fluoroalkyl iodide generated by the telomerization reaction is referred to as a fluoroalkyl iodide telomer in the present invention, and simply as a telomer in the present specification, in order to distinguish it from the fluoroalkyl iodide as the telogen. Also in the present specification, the fluoroalkyl iodide as the telogen is referred to as a fluoroalkyl iodide telogen or simply as a telogen; and tetrafluoroethylene is referred to as a tetrafluoroethylene taxogen or simply as a taxogen.

It is known that the above-described telomerization reaction proceeds by heating or by using a free-radical initiator (which may be referred to as a free-radical generator) (see, for example, Patent Citations 1-5 and Non Patent Citation 1).

In the case of heating, the telomerization reaction is conducted in the presence of a catalyst. As such a catalyst, zinc, magnesium, vanadium, rhenium, rhodium, ruthenium, platinum, or silver can be used (Patent Citation 3). Alternatively, copper can be used as a catalyst together with a co-catalyst of other transition metal(s) (Patent Citation 4).

Patent Citation 1: JP 6-305995 A
Patent Citation 2: U.S. Pat. No. 5,068,471 A
Patent Citation 3: JP 8-239335 A
Patent Citation 4: JP 8-239336 A
Patent Citation 5: JP 3800677 B2
Non Patent Citation 1: Qing-Yun Chen et al., "Copper-induced telomerization of tetrafluoroethylene with fluoroalkyl iodides", Journal of Fluorine Chemistry, 1987, vol. 36, pp. 483-489

DISCLOSURE OF INVENTION

Technical Problem

A telomerization reaction is a growing reaction in chain length, so that a reaction mixture obtained after the reaction includes various fluoroalkyl iodides (which may comprises a telogen and telomers) having different chain lengths. In order to avoid generating a telomer having a longer chain length than a desired chain length, it is considered to increase a ratio of the telogen to the taxogen, but there is a drawback causing a drop in a conversion ratio. Then, there are various proposals to obtain a fluoroalkyl iodide telomer having a desired chain length (or a degree of polymerization), efficiently.

For example, Patent Citation 5 describes that a reactor provided with a distillation column is used for a telomerization reaction in the presence of a free-radical initiator in the distillation column while a fluoroalkyl iodide telogen is refluxed.

However, the use of a free-radical initiator causes an unwanted side reaction(s) of a telogen with the free radical initiator to generate a by-product represented by the general formula of RfH. Further, the used free-radical initiator itself decomposes and generates by-products of the decomposition. Thus, it becomes necessary to separate and remove these by-products.

Any processes which has been proposed hitherto are not sufficient to obtain a fluoroalkyl iodide telomer of a desired chain length, efficiently.

The present invention aims to provide a novel process for producing a fluoroalkyl iodide telomer, which is able to obtain a fluoroalkyl iodide telomer having a desired chain length, efficiently.

Technical Solution

In one aspect of the present invention, there is provided a process for producing a fluoroalkyl iodide telomer, which comprises supplying a distillation apparatus with a fluoroalkyl iodide represented by a general formula RfI and tetrafluoroethylene which are used as a telogen and a taxogen, respectively, and subjecting these compounds to a telomerization reaction in the presence of a metal catalyst with heating in a reaction zone located in an intermediate part of the distillation apparatus to generate a fluoroalkyl iodide telomer represented by a general formula $Rf(CF_2CF_2)_nI$, and separating a fraction comprising the fluoroalkyl iodide telomer by distillation. With respect to the present invention, in the above formulae, Rf is a $C_{1-10}$ fluoroalkyl group (i.e. a fluoroalkyl group having a carbon number of 1-10), and n (degree of polymerization) is an integer of 1-4. Further, a "fraction comprising . . . " means a fluidic portion containing a prescribed substance as a main component, and preferably consisting substantially of the prescribed substance.

According to the production process of the present invention, the intermediate part of the distillation apparatus is utilized as the reaction zone, and thereby the telomerization reaction proceeds in the presence of a metal catalyst in this reaction zone, then the fraction comprising the fluoroalkyl iodide telomer can be moved from the reaction zone and separated by distillation depending on a boiling point of the fluoroalkyl iodide telomer having a desired chain length. Therefore, further growth in chain length (or polymerization) can be avoided, so that the fluoroalkyl iodides contained in the fraction thus obtained can show a sufficiently narrow distribution of chain length, and thus the fluoroalkyl iodide telomer having the desired chain length can be obtained with a high selectivity. Further, according to the production process of the present invention, since the telomerization reaction is conducted in the presence of the metal catalyst, a side reaction(s) generating unwanted by-products can be reduced. Especially, since a free-radical initiator is not used, neither a by-product represented by the general formula of RfH nor by-products by decomposition of the free-radical initiator itself are generated. Thus, there is no need to separate and remove these by-products.

Thus, according to the production process of the present invention, the fluoroalkyl iodide telomer having the desired chain length can be obtained, efficiently.

In one mode of the present invention, a temperature and a pressure in the reaction zone are a temperature and a pressure at which the fluoroalkyl iodide telogen is in a liquid condition. Therefore, the telomerization reaction proceeds in a liquid phase of the telogen, and its reaction temperature is lower than a reaction temperature of a gas phase telomerization reaction. This is industrially preferred and also advantageous in that decomposition of tetrafluoroethylene, which is thermally-labile, is not likely to be caused.

The production process of the present invention may further comprise separating a fraction comprising the tetrafluoroethylene by distillation and then returning it to the distillation apparatus so that the tetrafluoroethylene circulates through the reaction zone. Since the tetrafluoroethylene taxogen circulates through the reaction zone, the tetrafluoroethylene which is not consumed by the telomerization reaction can be reused.

In one mode of the present invention, the fluoroalkyl iodide telogen and the tetrafluoroethylene taxogen (which may comprise the form of fraction separated by distillation) are continuously supplied to the distillation apparatus, and the fraction comprising the fluoroalkyl iodide telomer is continuously taken out of the distillation apparatus. Therefore, the production process of the present invention can be conducted continuously, and this is industrially preferred.

In one mode of the present invention, the metal catalyst is silver or copper. The use of silver and copper as the metal catalyst in the present invention can show a high catalyst activity and bring about a high selectivity although they are at a relatively low price, so that this is industrially preferred.

ADVANTAGEOUS EFFECTS

In the present invention, a fluoroalkyl iodide telogen and a tetrafluoroethylene taxogen are supplied to a distillation apparatus and subjected to a telomerization reaction in the presence of a metal catalyst with heating in a reaction zone located in an intermediate part of the distillation apparatus to generate a fluoroalkyl iodide telomer, and a fraction comprising the fluoroalkyl iodide telomer is separated by distillation. According to the present invention, since the intermediate part of the distillation apparatus is utilized as the reaction zone, the telomerization reaction proceeds in this reaction zone. Then, when a fluoroalkyl iodide telomer of a desired chain length is generated, a fraction comprising it can be moved from the reaction zone and separated by distillation, and thereby the fluoroalkyl iodide telomer of the desired chain length can be obtained with a high selectivity. Further, according to the present invention, since the telomerization reaction is conducted in the presence of the metal catalyst, a side reaction(s) generating unwanted by-products can be reduced, effectively. Especially, since a free-radical initiator is not used, neither a by-product represented by the general formula of RfH nor by-products by decomposition of the free-radical initiator itself are generated. Thus, there is no need to separate and remove these by-products. Therefore, according to the present invention, the fluoroalkyl iodide telomer having the desired chain length can be obtained effectively.

BEST MODE FOR CARRYING OUT THE INVENTION

Hereinafter, one embodiment of the present invention will be described in detail.

At first, a telogen and a taxogen used as row materials, a metal catalyst and a distillation apparatus are prepared to be used in the present embodiment.

As the telogen, a fluoroalkyl iodide represented by the general formula RfI (wherein Rf is a $C_{1-10}$ fluoroalkyl group) can be used, and perfluoroalkyl iodide is preferred. Examples thereof may include 2-iodoperfluoropropane, 1-iodoperfluoroethane, 1-iodoperfluorobutane, 1-iodoperfluorohexane and so on. The telogen may be a single compound or a mixture of two or more selected from such compounds.

As the taxogen, tetrafluoroethylene is used.

As the metal catalyst, silver or copper, both of which are available at a relatively low price, is used in the present embodiment.

However, the present invention is not limited to them, and any metals may be used as the metal catalyst as long as they substantially have a catalytic action to the telomerization reaction between the fluoroalkyl iodide telogen and the tetrafluoroethylene taxogen. Examples of such metals may include copper, tin, zinc, magnesium, vanadium, rhenium, rhodium, ruthenium, platinum and silver; alloys or mixtures of two or more metals selected from the group consisting of these metals; or alloys resulted from addition of a little amount of transition metal(s) to one metal or two or more metals selected from the above group. As the transition metal (s), metals having no catalytic action by itself or having a very small catalytic action can be used, examples of them may include iron, nickel, chrome, molybdenum, tungsten, titanium and so on.

The form of the metal catalyst is not limited as long as the form is able to substantially exert a catalytic action to the telomerization reaction between the fluoroalkyl iodide telogen and the tetrafluoroethylene taxogen. For example, the form may be plate-like, block-like, filamentous, spherical powder, flake powder, sintered, or coating. Also, a metal catalyst supported on a carrier having or not having a catalytic action can be used. In particular, a metal catalyst having a large specific surface, e.g. a metal catalyst having a honeycomb or sintered structure is industrially preferred since it contributes to a smaller size of installation.

As the distillation apparatus, a distillation column (or tower) is used in the present embodiment. A reaction zone located in an intermediate part of the distillation column is filled with the metal catalyst in advance. Other parts of the distillation column can be filled with any suitable packing for separation by distillation.

However, the distillation apparatus used in the present invention is not limited to the distillation column, any apparatus can be preferably used, of which intermediate part can be used as a reaction zone for the telomerization reaction and by which as a whole a distillation operation can be conducted.

The fluoroalkyl iodide telogen and the tetrafluoroethylene taxogen are supplied to the above distillation column continuously. In the reaction zone, the telomerization reaction proceeds in the presence of the metal catalyst by heating (or in a heated condition).

The supply ratio of the telogen and the taxogen is not limited, but the ratio of the taxogen to the telogen may be, for example, about 0.01 to 10% by mole, preferably about 0.3 to 3% by mole. By using a larger amount of the taxogen than the amount of the telogen in this manner, a higher conversion ratio can be attained.

Regarding the supply of the telogen and the taxogen, these can be supplied to the distillation column in a state where the tetrafluoroethylene taxogen is dissolved in the fluoroalkyl iodide telogen. Alternatively, the fluoroalkyl iodide telogen and the tetrafluoroethylene taxogen may be supplied separately to the distillation column (preferably, at a position slightly lower than the reaction zone located in the intermediate part of the distillation column).

A low boiling point fraction comprising the tetrafluoroethylene taxogen is continuously taken out of the distillation column from its top and returned to the distillation column, so that the tetrafluoroethylene taxogen circulates through the reaction zone.

A pressure in the distillation column is preferably about −0.95 to 5 MPa (gauge pressure). When the pressure in the distillation column is not lower than about −0.95 MPa (gauge pressure), such pressure is, depending on a temperature in the distillation column and the used telogen, but generally higher than a vapor pressure of the telogen at the temperature by about 0.01 MPa or more. Since the tetrafluoroethylene is supplied to attain such pressure, a space time yield (i.e. yield per unit time and per unit mass of catalyst) is obtained. When the pressure in the distillation column is not lower than about 5 MPa (gauge pressure), a high selectivity of the telomerization reaction is obtained, and it is also advantageous in safety and cost effectiveness. However, it shall be noted that the telomerization reaction may proceed even at a pressure out of the above range.

A temperature in the distillation column may vary depending on the position, but at least the reaction zone is preferably maintained at a temperature depending on the pressure so that the fluoroalkyl iodide telogen is in a liquid state. Thus, the telomerization reaction can proceed in the liquid phase of the telogen. Since such reaction temperature is lower than a reaction temperature for a gas phase telomerization reaction, it is industrially preferred and also advantageous in that decomposition of tetrafluoroethylene, which is thermally-labile, is not likely to be caused.

The temperature of the reaction zone for the telomerization reaction is, depending on the pressure and so on, but for example about 60 to 160° C., and preferably about 80 to 140° C. When the temperature is not lower than about 60° C., a sufficient reaction velocity is obtained. When the temperature is not higher than 160° C., unwanted side reactions can be reduced effectively, and also this is safe and cost effective. Such side reactions may include, for example, a dimerizing reaction of generated fluoroalkyl radicals into a fluoroalkane, a reaction between telomers to generate fluoroalkane and iodine (iodine may cause corrosion of the reactor and clogging of a pile line and so on), a thermal decomposition of thermally-labile tetrafluoroethylene (this is especially unfavorable in view of safety). However, it shall be noted that the telomerization reaction may proceed even at a temperature out of the above range.

Thus in the reaction zone, the fluoroalkyl iodide telogen and the tetrafluoroethylene taxogen in the heated condition in the presence of the metal catalyst undergo a telomerization reaction according to the following formula to generate a fluoroalkyl iodide telomer.

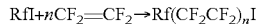

$$RfI + nCF_2=CF_2 \rightarrow Rf(CF_2CF_2)_nI$$

The generated fluoroalkyl iodide telomer is represented by the general formula $Rf(CF_2CF_2)_nI$ (wherein Rf is the same as Rf in the fluoroalkyl iodide telogen used as the reaction raw material, and n is an integer of 1-4).

This telomerization reaction is a growing reaction in chain length. When a fluoroalkyl iodide telomer having a desired chain length (n meaning a degree of polymerization is in a range from 1 to 4) is generated, a fraction comprising the fluoroalkyl iodide telomer is separated by distillation and taken out of the distillation column. The operation for the above separation can be conducted by distillation to separate a high boiling point fraction which corresponds to a boiling point of the fluoroalkyl iodide telomer having the desired chain length, since fluoroalkyl iodide telomers of different degrees of polymerization have different boiling points and they move according to distillation equilibrium depending on their own boiling points.

The high boiling point fraction comprising such fluoroalkyl iodide telomer is continuously taken out of the distillation column from its lower part (or bottom).

As described in the above, the present embodiment can produce the fluoroalkyl iodide telomer. Distribution of chain length of fluoroalkyl iodides in the high boiling point fraction obtained above is narrow, and thus the fluoroalkyl iodide telomer having the desired chain length can be obtained with a high selectively. In addition, since the present embodiment uses the metal catalyst and does not use a free-radical initiator, neither a by-product represented by the general formula of RfH nor by-products by decomposition of the free-radical initiator itself are generated, thus there is no need to separate and remove them. This production process is advantageous in safety and cost effectiveness, and preferably applied to an industrial-scale operation.

The present invention is heretofore described with respect to its one embodiment. However, the present invention is not limited to the above embodiment and may be modified variously. For example, the distillation column is used in the above embodiment, but in place of the distillation column an apparatus utilizing a tube-type reactor and so on can be used. Further, the fraction comprising the fluoroalkyl iodide telomer is taken out of the distillation column continuously and separately in the above embodiment. However, since the effects of the present invention can be obtained by moving (or transferring) the fluoroalkyl iodide telomer having the desired chain length from the reaction zone by distillation, similar (or equivalent) effects can be obtained by conducting the production process in a batch process where the fraction comprising the fluoroalkyl iodide telomer is taken out from the distillation column together with all other fractions in the form of a bottom product (reaction mixture).

EXAMPLES

Example

As a distillation apparatus, a stainless steel tube-type reactor having an outer diameter of ⅝ inch was used in the upright position. A reaction zone located in an intermediate part of the distillation apparatus was filled with 200 g of sintered compacts (1 mm in diameter and 10 mm in length) of copper spherical powder as a metal catalyst, and a part lower than the reaction zone was filled with packing for separation by distillation. Then, 692 g of 1-iodoperfluorobutane ($C_4F_9I$) was charged as a telogen into the bottom of the distillation apparatus.

Heating the distillation apparatus to give a temperature of 100° C. at the top of the distillation apparatus (top of the column), a pressure at the top of the distillation apparatus was maintained at 0.3 MPa (gauge pressure), and 1-iodoperfluorobutane was refluxed. Under this condition, tetrafluoroethylene was supplied as a taxogen over time to the distillation apparatus at a position slightly lower than the reaction zone of the distillation apparatus (tetrafluoroethylene became included in the reflux). When 36 g of tetrafluoroethylene was supplied in total, the supply thereof was stopped and then the distillation apparatus was cooled. Any liquid matter in the distillation apparatus (including a high-boiling point fraction) was taken out of the distillation apparatus as a bottom product (reaction mixture).

The reaction mixture thus obtained was subjected to composition analysis by gas chromatography. A conversion ratio of the telogen ($C_4F_9I$) and distribution in a degree of polymerization of fluoroalkyl iodides ($C_4F_9(CF_2CF_2)_nI$) in the reaction mixture calculated from the results of the analysis are shown in Table 1.

Comparative Example

Into a 230 mL stainless steel pressurized reactor which was equipped with a stirrer, 300 g of 1-iodoperfluorobutane ($C_4F_9I$) and 11 g of copper powder were charged as a telogen and a metal catalyst, respectively.

Heating the reactor to give a temperature of 100° C. to a liquid phase in the reactor, in order to maintain a pressure at 0.38 MPa (gauge pressure), tetrafluoroethylene was supplied as a taxogen to the reactor, appropriately and additively. When 50 g of tetrafluoroethylene was supplied in total, the supply thereof was stopped and then the distillation apparatus was cooled. A reaction mixture was taken out of the reactor.

The reaction mixture thus obtained was subjected to composition analysis by gas chromatography. A conversion ratio of the telogen ($C_4F_9I$) and distribution in a degree of polymerization of fluoroalkyl iodides ($C_4F_9(CF_2CF_2)_nI$) in the reaction mixture calculated from the results of the analysis are shown in Table 1.

TABLE 1

| | Telogen Conversion ratio (mol %) | Fluoroalkyl iodide Distribution (mol %) n value ($C_4F_9(CF_2CF_2)_nI$) | | | | |
|---|---|---|---|---|---|---|
| | | 1 | 2 | 3 | 4 | 5 |
| Example | 16 | 91 | 7.4 | 0.56 | 0.042 | — |
| Comparative Example | 50 | 85 | 13 | 1.6 | 0.18 | 0.022 |

In the table, the symbol "—" means that it was below the limit of detection.

Referring to Table 1, it was confirmed that the Example gave 1-iodoperfluorohexane (n=1), i.e. the fluoroalkyl iodide having the desired chain length, with a higher selectivity than that in the Comparative Example. It was also confirmed that the Example gave the fluoroalkyl iodides having a longer chain length (n=2 or more) than the desired chain length at a significantly smaller amount and had a very narrow distribution of chain length, compared with the Comparative Example.

Industrial Applicability

A fluoroalkyl iodide telomer(s) obtained by the present invention can be used as a raw material for a surfactant agent, a raw material for a oil- and water-repellant agent for treating fabrics, and so on.

The invention claimed is:

1. A process for producing a fluoroalkyl iodide telomer, which comprises
    supplying a distillation apparatus with a fluoroalkyl iodide represented by a general formula RfI, wherein Rf is a $C_{1-10}$ fluoroalkyl group, and tetrafluoroethylene which are used as a telogen and a taxogen, respectively, and subjecting these compounds to a telomerization reaction in the presence of a metal catalyst with heating in a reaction zone located in an intermediate part of the distillation apparatus to generate a fluoroalkyl iodide telomer represented by a general formula $Rf(CF_2CF_2)_nI$, wherein Rf is the same as defined above and n is an integer of 1-4;
    separating a fraction comprising the fluoroalkyl iodide telomer by distillation;
    separating a fraction comprising the tetrafluoroethylene by distillation; and
    then returning the tetrafluoroethylene fraction to the distillation apparatus so that the tetrafluoroethylene circulates through the reaction zone.

2. The process according to claim 1, wherein a temperature and a pressure in the reaction zone are a temperature and a pressure at which the fluoroalkyl iodide used as the telogen is in a liquid condition.

3. The process according to claim 1, wherein the fluoroalkyl iodide and the tetrafluoroethylene as the telogen and the taxogen, respectively are continuously supplied to the distillation apparatus; and the fraction comprising the fluoroalkyl iodide telomer is continuously taken out of the distillation apparatus.

4. The process according to claim 1, wherein the metal catalyst is silver or copper.

5. The process according to claim 3, wherein a temperature and a pressure in the reaction zone are a temperature and a pressure at which the fluoroalkyl iodide used as the telogen is in a liquid condition.

6. The process according to claim 5, wherein the metal catalyst is silver or copper.

* * * * *